(12) United States Patent
Winterot et al.

(10) Patent No.: US 6,823,079 B1
(45) Date of Patent: Nov. 23, 2004

(54) DEVICE FOR EXAMINING SAMPLES

(75) Inventors: Johannes Winterot, Jena (DE); Dietmar Schmidt, Bibra (DE); Dieter Schau, Nerkewitz (DE)

(73) Assignee: Carl Zeiss Jena GmbH, Jena (DE)

( * ) Notice: Subject to any disclaimer, the term of this patent is extended or adjusted under 35 U.S.C. 154(b) by 0 days.

(21) Appl. No.: 09/719,701

(22) PCT Filed: Mar. 23, 2000

(86) PCT No.: PCT/EP00/02551
§ 371 (c)(1),
(2), (4) Date: Feb. 27, 2001

(87) PCT Pub. No.: WO00/63678
PCT Pub. Date: Oct. 26, 2000

(30) Foreign Application Priority Data

Apr. 14, 1999 (DE) .......................... 199 16 749

(51) Int. Cl.[7] .................................................. G06K 9/00
(52) U.S. Cl. .................................. 382/133; 250/201.4
(58) Field of Search ................................ 382/128, 132, 382/133; 250/201.2, 201.4; 359/196, 205, 368, 383; 435/173.1

(56) References Cited

U.S. PATENT DOCUMENTS

| 5,674,698 | A | 10/1997 | Zarling et al. | ............. | 435/7.92 |
|---|---|---|---|---|---|
| 5,834,758 | A | 11/1998 | Trulson et al. | ............ | 250/201.2 |
| 5,874,219 | A | 2/1999 | Rava et al. | .................... | 435/6 |
| 5,885,531 | A | 3/1999 | Heffelfinger et al. | ..... | 422/82.05 |
| 6,143,535 | A | * 11/2000 | Palsson | .................... | 435/173.1 |
| 6,388,788 | B1 | * 5/2002 | Harris et al. | ................ | 359/196 |

FOREIGN PATENT DOCUMENTS

| WO | WO 97/35181 | 9/1997 | .......... G01N/21/64 |
|---|---|---|---|
| WO | WO 97/43611 | 11/1997 | ............. G01J/3/30 |
| WO | WO 98/53300 | 11/1998 | .......... G01N/21/00 |

* cited by examiner

Primary Examiner—Leo Boudreau
Assistant Examiner—Ryan J. Miller
(74) Attorney, Agent, or Firm—Reed Smith LLP

(57) ABSTRACT

An arrangement for examination of one or more specimens arranged in specimen vessels or on specimen carriers by transmitted light or incident light by imaging and/or detecting at least a portion of the specimen volume through the specimen vessel or specimen carrier by a CCD camera followed by an evaluating unit, wherein, advantageously, an incident illumination is likewise effected through the specimen vessel or specimen carrier and the illumination is used to excite specimen emission, preferably fluorescence excitation.

22 Claims, 6 Drawing Sheets

DEVICE FOR EXAMINING SAMPLES

BACKGROUND OF THE INVENTION

The invention is directed to an inverse automatic single-channel microscope with an autofocus system and with one or more specimen chambers or a specimen carrier.

The image of the specimen is evaluated by image analyzing software.

The specimens can be, for example, cells (in solution) at the bottom of microtiter plates (MTP), but can also be specimens on specimen carriers such as biochips, on plane-parallel plates of glass, silica glass or plastic. The MTPs or specimen carriers are preferably automated, but can also be supplied manually and the autofocus system focuses, for example, on the interface between the solution and MTP bottom. After the focusing and the selection of the excitation filter, the dyes are excited in the specimen, for example, in fluorescence detection, by means of XBO or HBO lamps. The fluorescent light of the specimen passes the selected emission filter and the specimen is imaged on the chip of the CCD camera.

After the image is recorded, excitation filters and emission filters, if any, are changed and a new image is recorded. Subsequently, the image is evaluated and an XY scanning table moves to the next image field or to the next MTP well, the autofocus is activated again and the sequence starts from the beginning.

The invention is described more fully with reference to the schematic drawings.

BRIEF DESCRIPTION OF THE DRAWINGS

In the drawings

FIG. 3 shows a view of the autofocus beam path in direction B in FIG. 2a;

DESCRIPTION OF THE PREFFERED EMBODIMENTS

Figure 1:
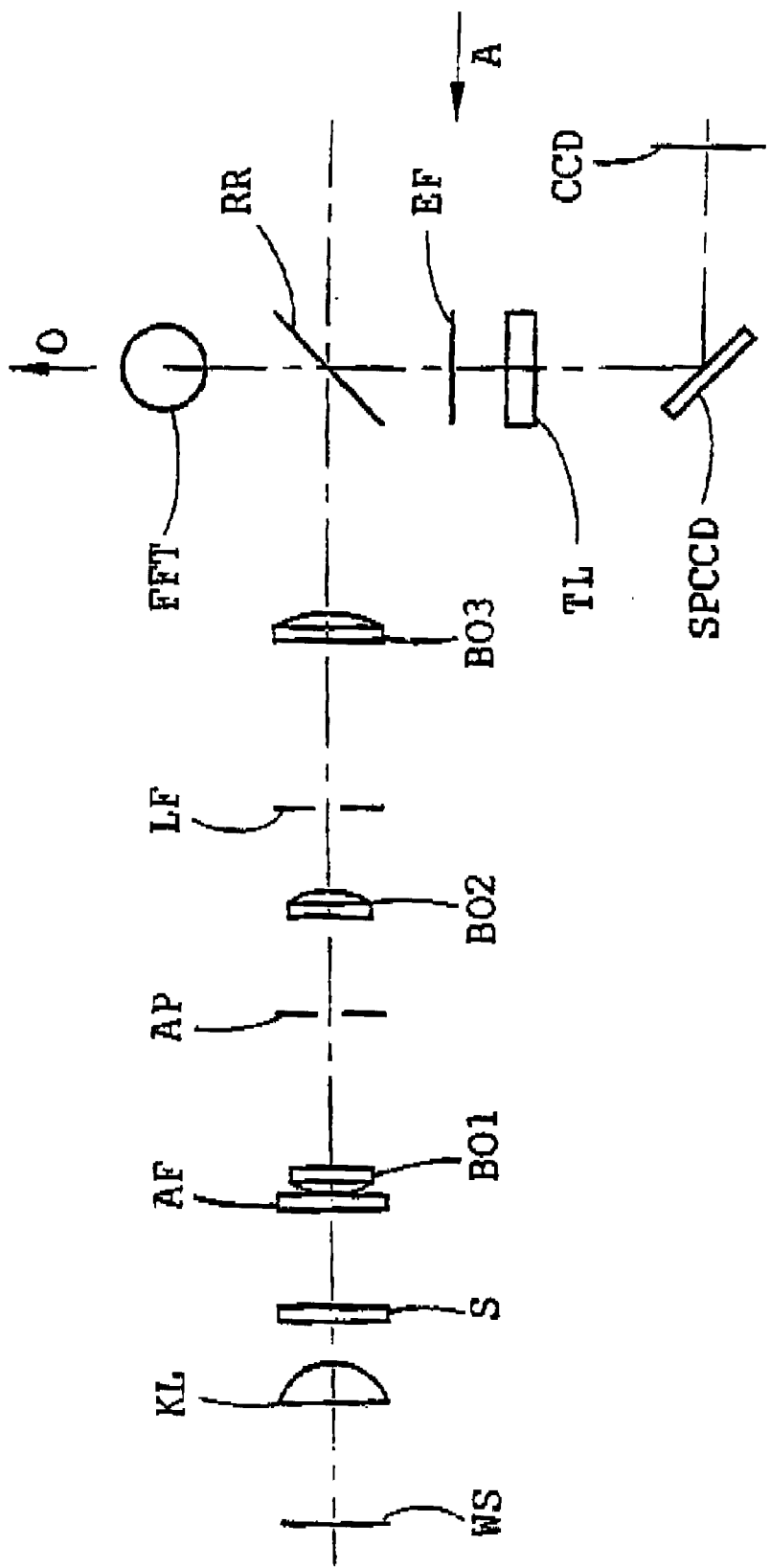
FIG. 1 shows the measurement beam path.

FIG. 1: For example, a light-conducting cable, not shown, is connected to a standard change location WS for the illumination or a lamp (white light source: xenon or mercury) can be provided.

The coupled in light reaches an in-coupling lens KL for collimation and travels through a shutter S, multiple-lens illumination optics BO1–3, an aperture stop AP between BO1 and BO2 and a field diaphragm LF between BO2 and BO3 to a reflector turret RR, with preferably exchangeable beam splitters for splitting the excitation beam path in the direction of the objective O and the evaluating beam path in the direction of the receiver CCD. For fluorescence detection, an excitation filter AF is arranged in front of the in-coupling optics BO1. Emission filters EF are provided in the evaluating beam path to block the reflected or elastically scattered excitation light.

Advantageous wavelength ranges for AF, EF are 350–700 nm (excitation of dyes) and 420–800 nm (emission of dyes).

The filters AF, EF are exchangeable or can also be swiveled out for other applications.

The evaluating light reaches the CCD camera via a tube lens TL and a mirror SP CCD.

Figure 2:
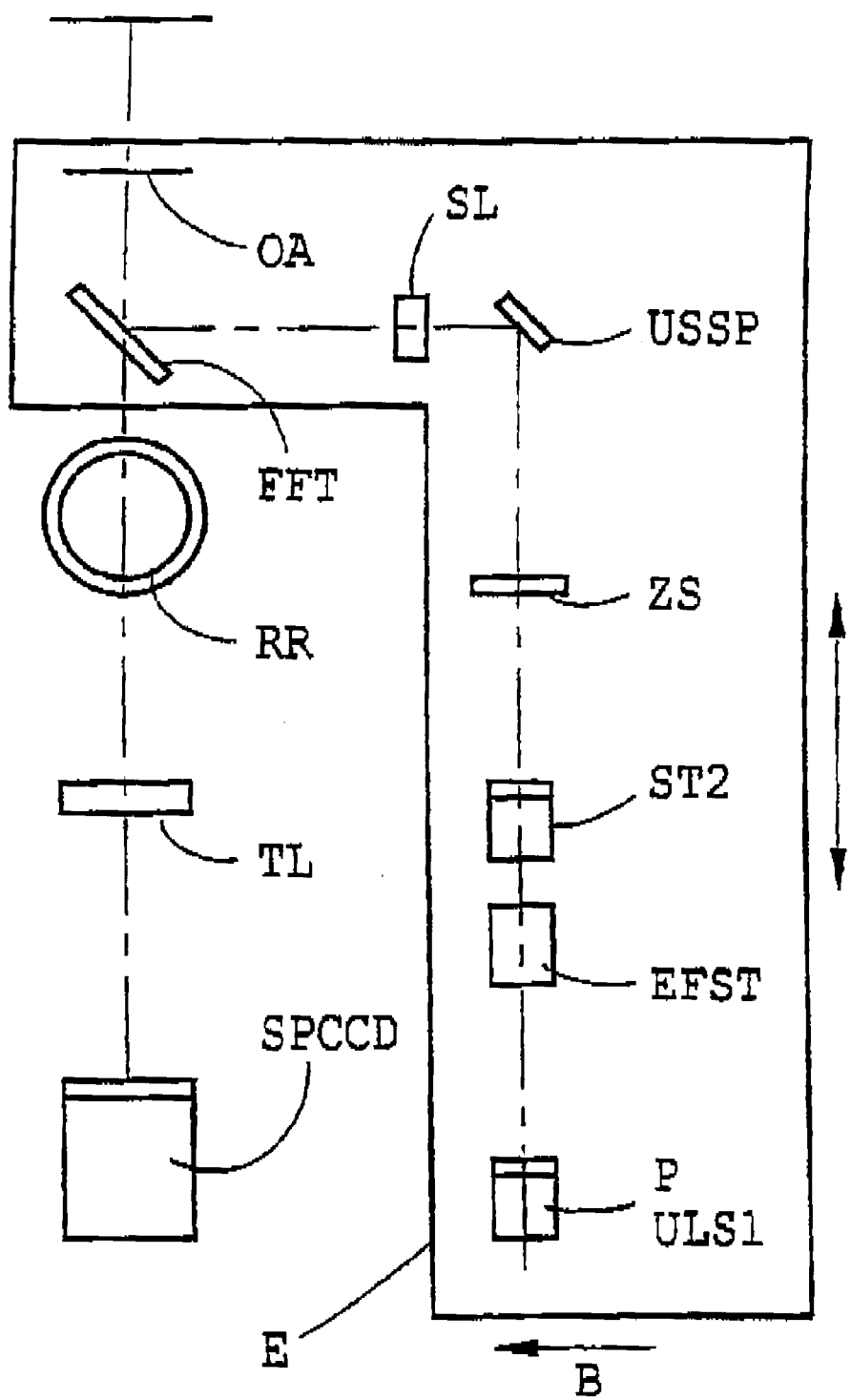
FIG. 2 shows a view of the autofocus beam path in direction A in FIG. 1.
Figure 3:
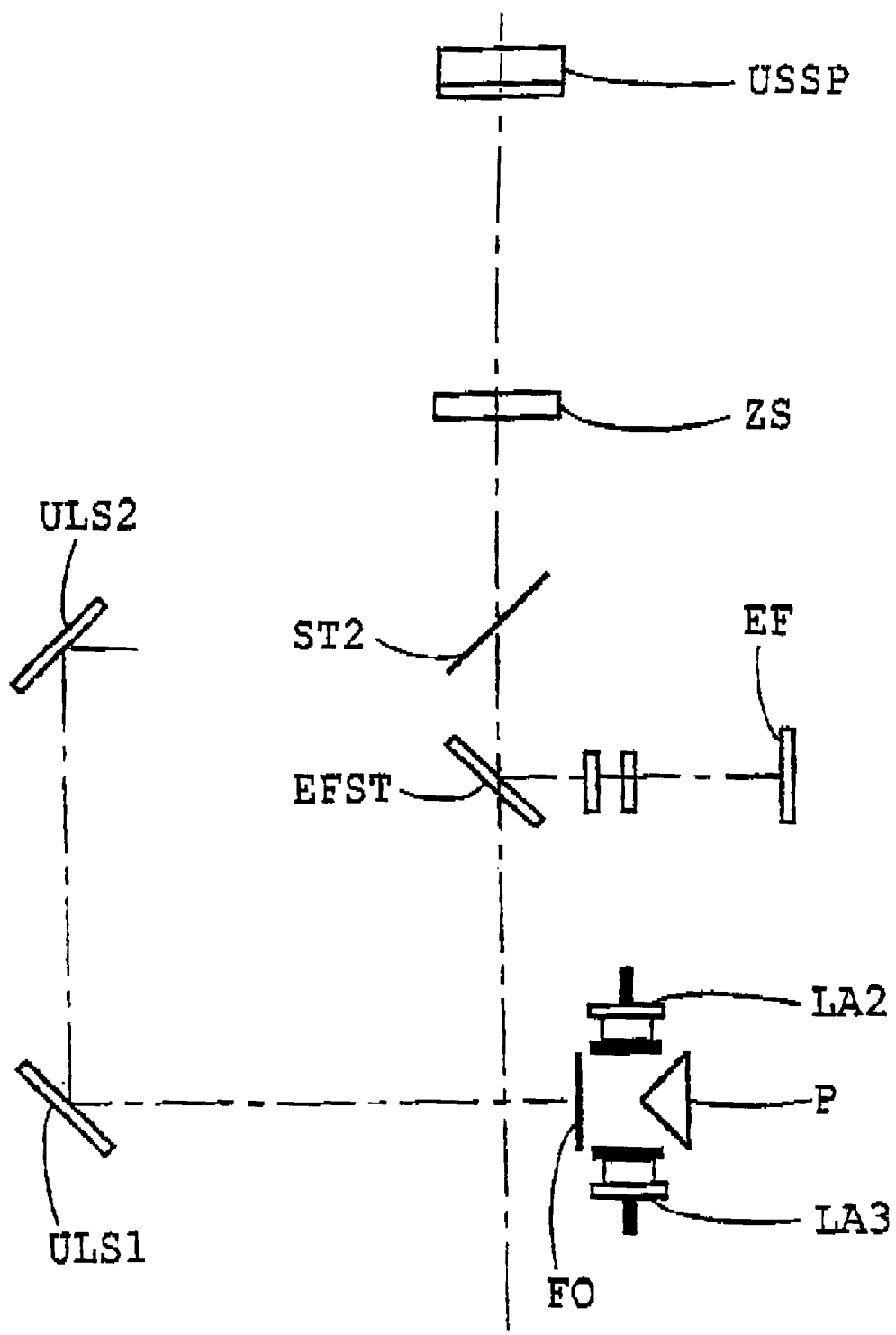

The advantageous autofocus beam path which is coupled in via a color splitter FT between RR and O is described with reference to FIGS. 2, 3 and 6.

The unit E, shown in dashed lines, which contains the objective, the in-coupling color splitter FT and the autofocus beam path is displaced at right angles to the object plane for focus correction.

One of the laser light sources LA2, LA3 (the other is switched off) is coupled in parallel via a prism P and is focused via optics FO. Two laser light sources can be advantageous when the objective O is exchangeable and, because of the different exit pupils of the objectives, a different axial offset of the light source image is to be adjusted via different positions of the laser relative to the prism P.

The laser light travels via deflecting mirror ULS1, 2, a partially transparent mirror ST2, a dispersive lens ZS, a deflecting mirror USSP, a collecting lens SL shown in microtiter plate MTP and in front of the objective contact face OA in the direction of the objective O.

The color splitter is advantageously highly transmissive over a wide spectral range (350–780 nm), i.e., from the short-wave excitation light of an HBO lamp to the long-wave emission spectrum of red dyes, but highly reflective for wavelengths over 800 nm, i.e., for the light of the autofocus laser.

It is particularly advantageous that the autofocus beam path is coupled in directly before the microscope objective because when there are only a few vertical optical interfaces this results in low light losses and accordingly increased accuracy and the color splitter FFT can pass fluorescent light without hindrance over a wide spectral range outside the IR wavelength used for autofocus and therefore only the reflections of the IR focusing laser are reflected back into the autofocus beam path.

Due to the fact that in-coupling is located after the illumination in the illumination direction, the autofocus is independent from the adjustment state, e.g., of the in-coupling elements for the illumination.

Because of the low intensity of the fluorescent light which can be excited in the specimen, conventional autofocus methods based on the evaluation of image contrast are not suitable, since several seconds would have to be integrated for each individual image in order to obtain a regulating signal that can be evaluated at all. With the present process, focusing times of less than a second can be realized, which is advantageous with respect to total measurement time.

The light reflected at the MTP is detected via the receiver beam splitter EFST and the receiver EF.

Figure 4:
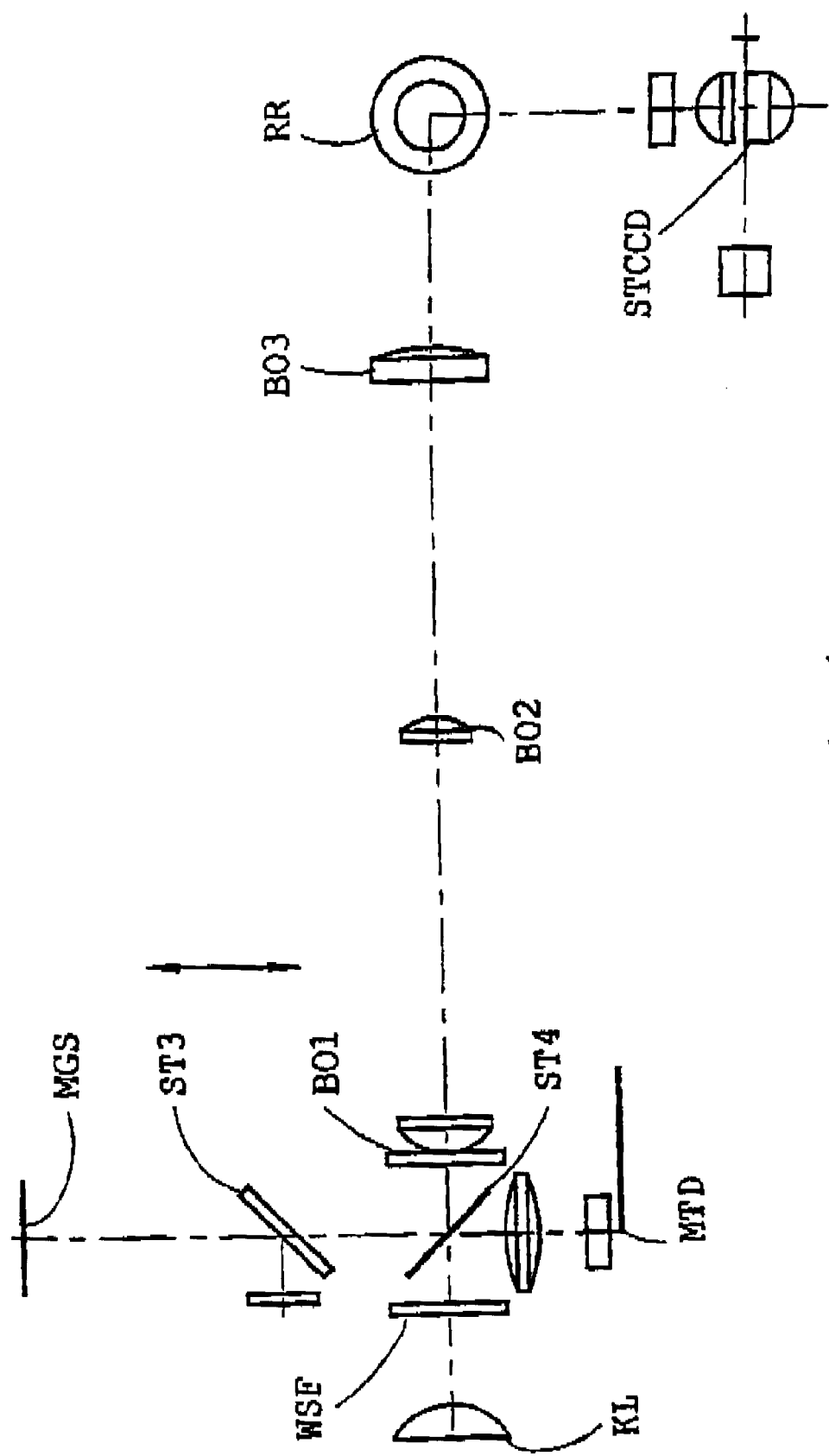
FIG. 4 shows an adjustment device for the light source in the illumination beam path.

The alignment or adjustment for the coupling in of a light source is shown in FIG. 4.

Following the reflector turret in the direction of the mirror SP CCD, the beam path is turned by 90 degrees about the optical axis of the in-coupling.

In one adjustment position, the light from the light source is deflected onto a ground glass plate MGS by the displacement of mirror ST3 and beam splitter ST4 after the in-coupling lens KL in the illumination beam path shown in FIG. 1 when the mirror SP3 is inserted, so that the position of the light source image can be aligned to the optical axis by the in-coupling lens KL in the illumination beam path shown in FIG. 1 when the mirror SP3 is inserted, so that the position of the light source image can be aligned to the optical axis by the operator. Also, when coupling in via the light-conducting fiber, this arrangement can be used to monitor the position. In the normal position when the beam splitter ST4 is inserted, a small portion of the light intensity (about 4%) for detecting and regulating the light output reaches a monitor diode MTD. A heat protection filter WSF is arranged in front of the beam splitter.

Figure 5:
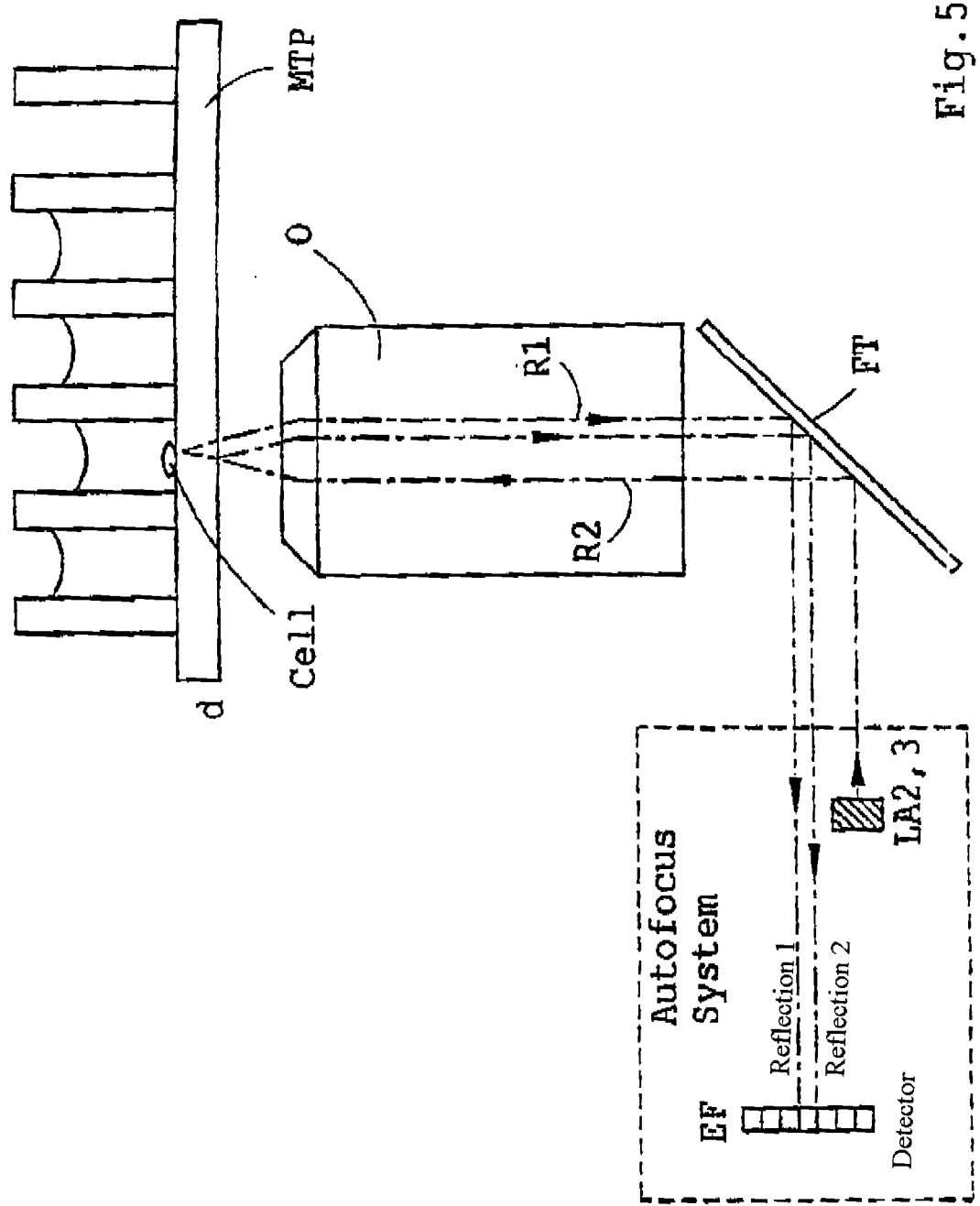
FIG. 5 shows the beam path with autofocus.

FIG. 5: Autofocus system. An autofocus system is advantageous for accurate focusing, for example, on the bottom of the MTP because, although the latter is parallel per se, it is sharply curved in general (order of magnitude 200–300 $\mu$m), so that a fixed focus does not function.

The speed of the autofocus has the highest priority. After loading a new plate and setting up and focusing for the first time, the time for focusing (required, e.g., after the plate has been moved in order to evaluate anther droplet) is appreciably less than 1 sec.

It can be seen from FIG. 5 that reflections R2, R1 of the laser of the autofocus are formed of the underside of the plate and also the top of the plate and can be recorded on the receiver EF.

The reflections run at a lateral offset; depending on the thickness of the plate, both signals are received on the CCD line or, with greater thicknesses, the reflections are so far apart that only one reflection is detected on the CCD. When the objective is moved toward the object from a position which is far away from the object, the lower reflection appears first. When both reflections are detected, the stronger reflection on the top can be distinguished from the weaker reflection on the bottom based on the intensity.

With a given thickness, it can also be determined whether only one reflection or both reflections will be located on the receiver EF due to the arrangement.

When both reflections occur, the stronger reflection, i.e., the higher peak, is ignored and only the maximum of the weak peak is used for focus monitoring by means of a regulating algorithm. In every case, with two existing reflections it can be determined from the geometry of the arrangement which reflection originates from the underside of the plate.

The characteristics of the optical reader system (objective parameters) on the one hand and of the object (thickness of the bottom of the microtiter plate) on the other hand show that one or two reflections are imaged by the object on the detector of the autofocus system (CCD line) automatically when the object is located in the focal position.

Case A: Two Reflections to be Expected Simultaneously on CCD Line (from Upper Side and Underside of Plate) from Plate Thickness Regulating Sequence:

1. Analysis of the curve imaged on the CCD line based on maxima, minima and reciprocal values. Subpixel resolution leads to increased accuracy.

2. It is determined from the results whether there are one or two reflections.

3. When there are two reflections, the adjustment or correcting value for the focusing drive is calculated from the offset of the relevant reflection to the defined focal point on the CCD line.

4. If only one of the two reflections is imaged on the line, the position of the existing reflection relative to the capture range boundary for the first movement in the direction of the focal point is relevant until the second reflection appears on the CCD line.

Case B: Only One Reflection on the CCD Line

Regulating Sequence:

1. Analysis of the curve imaged on the CCD line based on maxima, minima and reciprocal values. Subpixel resolution leads to increased accuracy.

2. With locked in control loop, the correcting value for the focusing drive is calculated from the offset of the reflection to the defined focal point on the CCD line.

3. If there is no reflection on the CCD line at the starting time of the control loop or it is not ensured that the reflection of the inside of the microtiter plates is located in the capture area of the control loop, a reflection search must initially be carried out from a defined Z-position in the direction of the microtiter plate.

The autofocus can also be corrected electronically in a particularly advantageous manner by several micrometers by focusing into the specimen solution (the specimen) rather than on the bottom (or on the specimen carrier). This is carried out either by means of an automatic electronic correction value of the autofocus before the objective control or by displacement of the objective itself which is adjusted automatically by a small amount after focusing.

Figure 6:
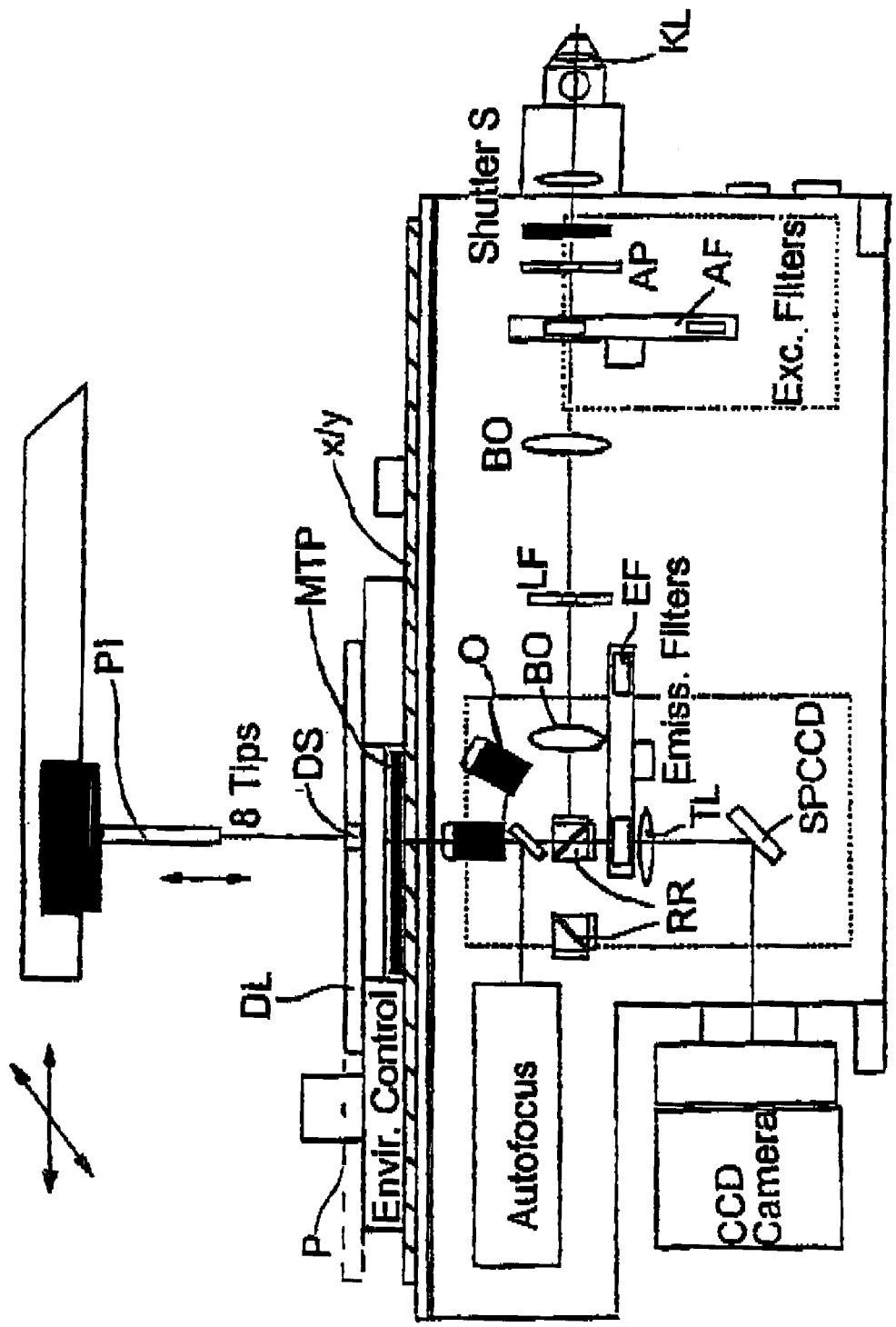
FIG. 6 shows a schematic overall arrangement.

FIG. 6 shows an overall arrangement with a microtiter plate MTP on an X/Y table and a pipettor for introducing specimens into the MTP and the optical arrangement in FIGS. 1–5, shown schematically in this instance.

While the foregoing description and drawings represent the present invention, it will be obvious to those skilled in the art that various changes may be made therein without departing from the true spirit and scope of the present invention.

Reference Numbers standard change location WS
in-coupling lens KL
illumination optics BO
aperture stop AP
shutter S
field diaphragm LF
excitation filter AF
emission filter EF
reflector turret RR
color splitter FFT
objective O
mirror for CCD SPCCD
CCD camera
lasers LA2, LA3 for autofocus
prism P
focusing optics FO
deflecting mirror ULS 1, 2
beam splitter ST2
dispersive lens ZS
receiver beam splitter EFST
receiver EF
deflecting mirror USSP
beam splitter ST3, 4
monitor diode MTD
ground glass plate MGS
heat protection filter WSF
pipettor PI
microtiter plate MTP

What is claimed is:

1. An arrangement for examination of one or more specimens arranged in specimen vessels, a plurality of specimen vessels being located on a microtiter plate, by transmitted light or incident light comprising: a CCD camera for imaging and/or detecting fluorescence signals coming from at least a portion of the specimen volume through the specimen vessel in response to a fluorescence excitation beam; an evaluating unit responsive to said CCD camera; and an autofocus system for accurate focusing of the imaging, which is arranged immediately downstream of an imaging objective in the imaging direction; said autofocus system further illuminating the specimen vessel from below by at least one focusing beam; a CCD receiver for evaluating the beam components reflected by the specimen vessel to locate the boundary of the specimen vessel; and said autofocus system further generating a correction value to focus on the specimen or into the interior of the specimen vessel during focusing and when the boundary of the specimen vessel is located; said imaging and/or detection being done on a side remote of a filling or charging device through said specimen vessel by said CCD camera followed by said evaluating unit.

2. The arrangement according to claim 1, wherein an incident illumination is transmitted through the specimen vessel.

3. The arrangement according to claim 1, wherein an illumination is used to excite specimen emission.

4. The arrangement according to claim 1, wherein a splitting of an excitation beam path and imaging beam path is carried out by at least one beam splitter.

5. The arrangement according to claim 4, wherein the autofocus system is inserted between an imaging objective and beam splitter.

6. The arrangement according to claim 1, wherein insertion of the autofocus is carried out by a color splitter.

7. The arrangement according to claim 6, wherein the color splitter is highly transmissive over a wide spectral range (350–780 run), but highly reflective for wavelengths over 800 nm, particularly for the light of an autofocus laser.

8. The arrangement according to claim 1, wherein the autofocus system is inserted in the direction of illumination after a light source or in-coupling location for the illumination.

9. The arrangement according to claim 1, with focusing on cells at or in the vicinity of the bottom of the specimen vessel.

10. The arrangement according to claim 1, with an X/Y table for introducing different specimen vessels into an excitation beam path.

11. The arrangement according to claim 1, wherein a separate focusing is carried out for each specimen.

12. The arrangement according to claim 1, further comprising an arrangement for adjustment during the coupling in of a light source for specimen illumination, wherein the light of the light source is deflected onto a ground glass plate by an insertable mirror in one adjustment position, so that the position of the light source image can be aligned to the optical axis.

13. The arrangement according to claim 12, wherein a small portion of light intensity reaches a monitor diode for detection and regulation of light output in a normal position with an inserted beam splitter.

14. The arrangement of claim 13, wherein the small portion of the light intensity is about 4%.

15. The method according to claim 1, wherein beam components originating from different interfaces or boundary layers of the specimen vessel are identified and focusing is effected on a boundary layer.

16. The method according to claim 1, wherein a focusing is carried out on the vessel bottom.

17. The method according to claim 1, wherein the specimen vessel is a microtiter plate.

18. An arrangement for examination of specimens arranged in a specimen carrier comprising: a CCD detection device for detecting fluorescence signals coming from the specimen in response to a fluorescence excitation beam; an evaluating unit responsive to the CCD detection device; and an autofocus system arranged immediately downstream of an imaging objective in an imaging direction, said autofocus system providing a focusing beam to illuminates the specimen carrier from below; a CCD receiver for evaluating beams reflected by the specimen carrier to locate the boundary of the specimen carrier; and said autofocus system further generating a correction value to focus on the interior of the specimen when the boundary of the specimen carrier is located.

19. The arrangement according to claim 18, wherein the CCD detection device is arranged on a side remote of a filling device that fills the specimens in the specimen carrier.

20. The arrangement according to claim 18, wherein the autofocus system receives two reflections representing an upper side and a lower side of the specimen carrier and generates the correction value based on the two reflections.

21. A method of examining specimens arranged in a specimen carrier, comprising:

illuminating a focusing beam on a lower surface of the specimen carrier by an autofocus system arranged immediately downstream of an imaging objective in an imaging direction;

evaluating the boundary location of the specimen carrier from the focusing beam reflected by the specimen carrier;

generating a correction value to focus on the interior of the specimen; and detecting by a CCD detection device fluorescence signals coming from the specimen in response to a fluorescence excitation beam.

22. The method according to claim 21, wherein the step of evaluating includes receiving two reflections representing an upper side and a lower side of the specimen carrier, and the correction value is generated based on the two reflections.

* * * * *